(12) United States Patent
Barbour

(10) Patent No.: US 11,369,802 B2
(45) Date of Patent: Jun. 28, 2022

(54) METHODS AND SYSTEMS FOR THE THERAPEUTIC APPLICATION OF LASER AND CANNABIDIOL TO THE SKIN

(71) Applicant: Michael Barbour, Missouri City, TX (US)

(72) Inventor: Michael Barbour, Missouri City, TX (US)

( * ) Notice: Subject to any disclaimer, the term of this patent is extended or adjusted under 35 U.S.C. 154(b) by 0 days.

(21) Appl. No.: 17/021,641

(22) Filed: Sep. 15, 2020

(65) Prior Publication Data

US 2021/0244963 A1 Aug. 12, 2021

Related U.S. Application Data

(60) Provisional application No. 62/975,499, filed on Feb. 12, 2020.

(51) Int. Cl.
*A61N 5/06* (2006.01)
*A61K 36/185* (2006.01)

(52) U.S. Cl.
CPC .......... *A61N 5/0616* (2013.01); *A61K 36/185* (2013.01); *A61N 2005/0644* (2013.01); *A61N 2005/0658* (2013.01)

(58) Field of Classification Search
CPC .................. A61N 5/0616; A61N 5/067; A61N 2005/0658; A61N 2005/0644; A61N 2005/0659; A61K 36/185; A61K 31/352
See application file for complete search history.

(56) References Cited

U.S. PATENT DOCUMENTS

| | | |
|---|---|---|
| 4,612,604 A | 9/1986 | Schlyter |
| 4,686,979 A | 8/1987 | Gruen et al. |
| 4,686,986 A | 8/1987 | Fenyo et al. |
| 4,836,203 A | 6/1989 | Muller et al. |
| 4,930,504 A | 6/1990 | Diamantopoulos et al. |
| 4,973,848 A | 11/1990 | Kolobanov et al. |
| 4,989,605 A | 2/1991 | Rossen |
| 5,011,483 A | 4/1991 | Sleister |
| 5,029,581 A | 7/1991 | Kaga et al. |
| 5,050,597 A | 9/1991 | Daikuzono |
| 5,062,842 A | 11/1991 | Tiffany |
| 5,071,416 A | 12/1991 | Heller et al. |
| 5,123,902 A | 6/1992 | Muller et al. |
| 5,130,997 A | 7/1992 | Ortiz et al. |
| 5,150,704 A | 9/1992 | Tatebayashi et al. |
| 5,161,526 A | 11/1992 | Hellwing et al. |
| 5,217,455 A | 6/1993 | Tan |
| 5,222,953 A | 6/1993 | Dowlatshahi |

(Continued)

OTHER PUBLICATIONS

Operating Guide ML830® Smart Laser (Year: 2013).*

(Continued)

*Primary Examiner* — Nathan J Jenness
(74) *Attorney, Agent, or Firm* — Michael S. McCoy; Amatong McCoy LLC

(57) ABSTRACT

A method for applying cannabidiol onto and into the skin is provided. The method includes applying cannabidiol onto skin and irradiating the skin and the cannabidiol with a laser light. The laser light has a wavelength ranging from 800 nm to 870 nm. The irradiating of the skin with the laser light results in at least some of the cannabidiol penetrating into the skin. The cannabidiol can be provided in a kit with a laser emitting tool.

16 Claims, 7 Drawing Sheets

(56) References Cited

U.S. PATENT DOCUMENTS

| | | | |
|---|---|---|---|
| 5,231,984 A | | 8/1993 | Santana-Blank |
| 5,246,436 A | | 9/1993 | Rowe |
| 5,312,395 A | | 5/1994 | Tan et al. |
| 5,344,434 A | | 9/1994 | Talmore |
| 5,464,436 A | * | 11/1995 | Smith .................. A61N 5/0616<br>606/13 |
| 6,214,035 B1 | * | 4/2001 | Streeter ................ A61N 5/0601<br>607/89 |
| 10,398,776 B1 | * | 9/2019 | Chah ...................... A61K 31/05 |
| 2002/0111377 A1 | * | 8/2002 | Stinchcomb ......... A61K 31/353<br>514/468 |
| 2008/0319510 A1 | * | 12/2008 | Simpson .............. A61N 1/3787<br>607/59 |
| 2011/0125226 A1 | * | 5/2011 | Lytle .................... A61N 5/0613<br>607/88 |

OTHER PUBLICATIONS

Mokoena et al. "Enhancing Breast Cancer Treatment Using a Combination of Cannabidiol and Gold Nanoparticles for Photodynamic Therapy" Int. J. Mol. Sci. 2019, 20, 4771 (Year: 2019).*

* cited by examiner

METHODS AND SYSTEMS FOR THE THERAPEUTIC APPLICATION OF LASER AND CANNABIDIOL TO THE SKIN

CROSS-REFERENCE TO RELATED PATENT APPLICATIONS

The present application claims the benefit of U.S. Provisional Patent Application No. 62/975,499, filed Feb. 12, 2020, entitled "METHODS AND SYSTEMS FOR THE THERAPEUTIC APPLICATION OF LASER LIGHT AND CBD OIL TO THE SKIN", the entirety of which is incorporated herein by reference.

FIELD

The present disclosure relates to apparatus and systems for applying laser and cannabidiol (CBD) onto tissue (e.g., skin), and to methods of making and using the same.

BACKGROUND

Cannabidiol oil is a non-intoxicating cannabis extract that is used to treat many ailments, including epileptic seizures, anxiety, inflammation, and insomnia to name just a few. Cannabidiol oil is taken via oral ingestion, topical applications, and even inhalation via vaporizing.

Low level laser therapy (LLLT) is used to deliver photons to tissues below the skin surface without causing adverse effects from superficial heating. Some LLLT methods and systems are capable of providing laser light that penetrates relatively deeply into tissue without harming the surrounding tissues and, thus, optimizing the treatment of a patient using LLLT, such as is disclosed in U.S. Pat. No. 5,464,436 ('436 Patent), the entirety of which is incorporated herein by reference.

It would be desirable to have methods and systems for synergistically combining LLLT treatments with CBD oil treatments to provide novel therapeutic treatments to patients.

BRIEF SUMMARY

Some embodiments of the present disclosure include a method for applying cannabidiol. The method includes applying cannabidiol onto a tissue. The method includes irradiating the tissue and the cannabidiol applied to the tissue with a laser light. The laser light has a wavelength sufficient to cause absorption of at least some of the cannabidiol into the tissue.

Some embodiments of the present disclosure include a kit for applying cannabidiol. The kit includes cannabidiol and a laser emitting tool. The laser emitting tool includes at least one diode. The laser emitting tool is actuable to emit laser light from the at least one diode at a wavelength sufficient to cause cannabidiol to absorb into tissue.

BRIEF DESCRIPTION OF THE DRAWINGS

So that the manner in which the features and advantages of the systems, apparatus, and methods may be understood in more detail, a more particular description may be had by reference to the embodiments which are illustrated in the appended drawings that form a part of this specification. It is to be noted, however, that the drawings illustrate only various exemplary embodiments and are therefore not to be considered limiting of the disclosed concepts as it may include other effective embodiments as well.

Figure 1:
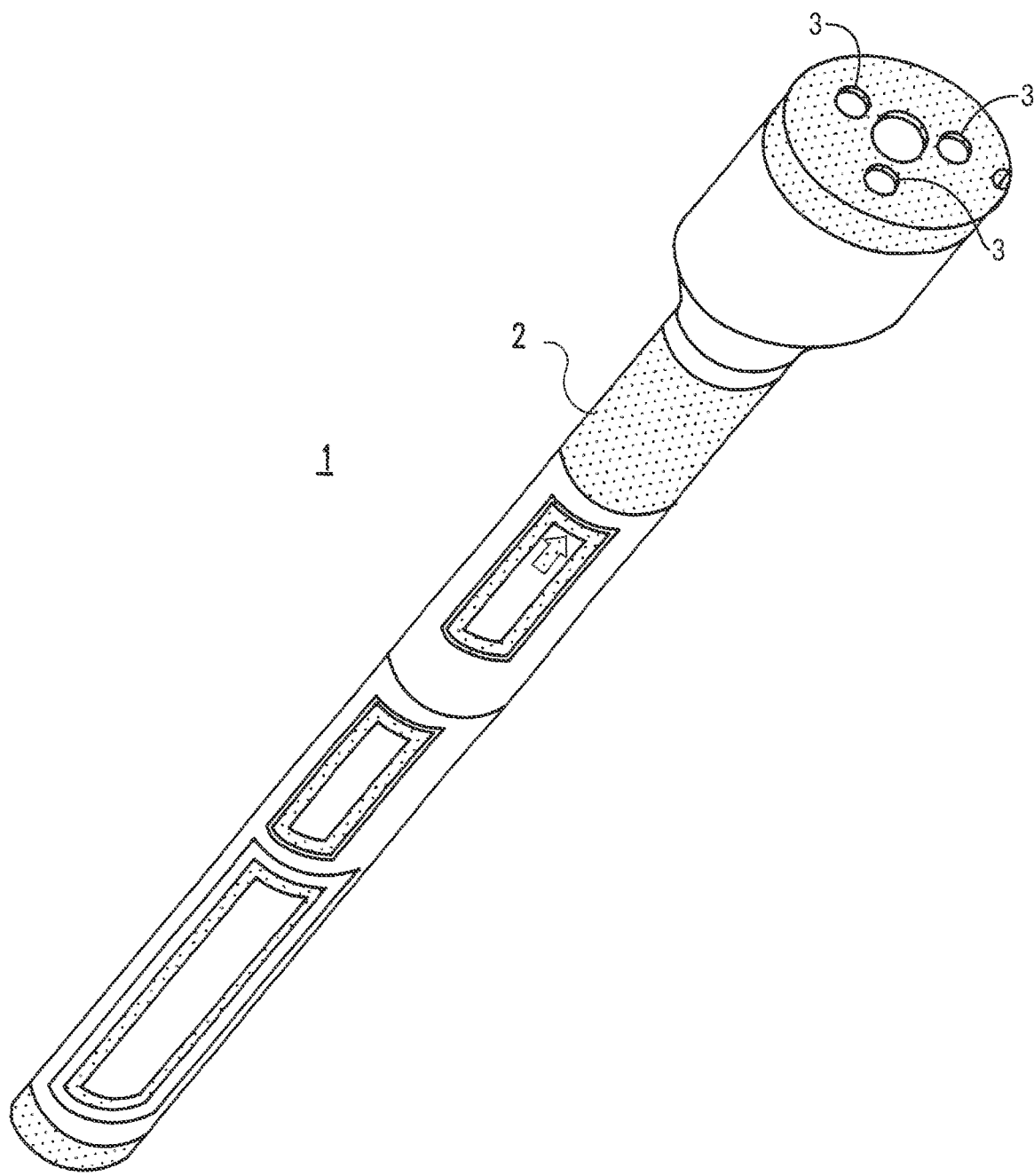
FIG. 1 is a perspective view of a handheld laser tool for performing low level laser therapy on a patient.

Systems, apparatus, and methods according to present disclosure will now be described more fully with reference to the accompanying drawings, which illustrate various exemplary embodiments. Concepts according to the present disclosure may, however, be embodied in many different forms and should not be construed as being limited by the illustrated embodiments set forth herein. Rather, these embodiments are provided so that this disclosure will be thorough as well as complete and will fully convey the scope of the various concepts to those skilled in the art and the best and preferred modes of practice.

DETAILED DESCRIPTION

Certain aspects of the present disclosure include apparatus, systems, and methods for using laser light in combination with CBD to provide therapeutic treatment to tissues including the skin. As used herein, "tissue" is in reference to aggregates of cells, together with intercellular substance, that form structural material of an animal (e.g., living tissue of an animal, such as skin).

Low Level Laser Therapy

Some embodiments of the present disclosure include systems and methods for performing therapy on a patient for symptomatic relief and management of pain and adjunctive treatment in the management of traumatic acute pain. More particularly, the present disclosure includes systems and methods for performing low level laser therapy on a patient.

Without being bound by theory, biological systems require energy for continued metabolism, function and repair. Normal cellular metabolism provides chemical energy and homeostatic heat for nominal biological system function. When injury to a biological system (e.g., organs, tissues, cells) occurs, usual metabolic systems may not be able to maintain homeostatic energy requirements. Biological systems include enzymes and membranes which selectively allow certain ions, proteins, carbohydrates, etc., to function and move in and out of the cells. Several mechanisms, including receptor mediated movement, allow these enzyme systems and membranes to perform their selective function. Injury to these enzyme and membrane systems causes membrane de-stabilization and loss of selective function. This membrane injury can result in swelling and edema. It is believed that, in many cases, the addition of energy to these enzyme and membrane systems can facilitate the re-stabilization and return of other normal functions of the organ, tissue, or cell containing the enzyme/membrane system.

Thus, some embodiments of the present disclosure includes systems and methods for treating a patient, including: (1) providing a laser source for emitting a laser light; (2) diagnosing an afflicted area of the patient; (3) delivering the laser light to the afflicted area for at least one treatment cycle, the laser source being operable on the afflicted area at a level of, for example, 1 Joule/cm$^2$ per treatment cycle; (4) monitoring the afflicted area after the treatment cycle has been completed; and (5) repeating the steps of diagnosing and delivering the laser light to the afflicted area, as needed, based on the monitoring step. Each treatment cycle can have a duration of 33 seconds and the wavelength of the laser light may be within a range of 800-870 nm, such as 830 nm. Without being bound by theory, it is believed that laser light at the wavelength of 830 nm is capable of penetrating relatively deeply into tissues without having destructive effects which occur when using "hot lasers."

FIG. 1 depicts handheld laser tool 1 for performing LLLT in accordance with some embodiments. Handheld laser tool 1 may be a commercially available tool, such as those available from MICROLIGHT® Corporation of America, of Sugarland, Tex., such as the 830 laser. Tool 1 may be a single or multiple-diode laser tool, depending upon the treatment protocol to be performed. FIG. 1 illustrates a multiple-diode tool (e.g., GaAlAs laser diodes) for issuing a laser light having a wavelength of 830 nanometers. Tool 1 may be battery-operated, and may produce a laser wavelength of ranging from 800 to 870 nm, and may have a laser power of from 30 to 70 mW continuous wave (cw). In one example, tool 1 may deliver 1 Joule of energy within a treatment cycle duration of 33 seconds. Tool 1 may have a lens system, such that the beam diameter of the laser can be formed to be approximately 3 mm$^2$ (e.g., a 1 mm×3 mm rectangle). The dimensions of one exemplary embodiment of tool 1 are approximately 2.1 cm in diameter by 20.3 cm in length, with a weight of approximately 125 grams. The total laser energy deliverable from tool 1, with a fully charged battery, may be more than 100 Joules. The size and shape of the tool 1 can be modified depending upon the patient (e.g., human or animal) to be treated.

The power output of tool 1 can be tested. In one exemplary embodiment, to test the power output of tool 1, tool 1 is placed into a probe sensor 22 port located on a recharger (shown and described below with reference to FIG. 2) and held steady during testing. Switch 2 may be activated, such as by squeezing the surface of tool 1 at switch 2, which activates an audible sound that continues for 33 seconds. At the completion of 33 seconds, there is a short, continuous, and audible tone and the meter reading is noted. The output is measured in milliwatts. In the embodiment of FIG. 1, tool 1 includes a plurality (here three) of diodes 3 that emit laser light upon activation of tool 1.

Figure 2:
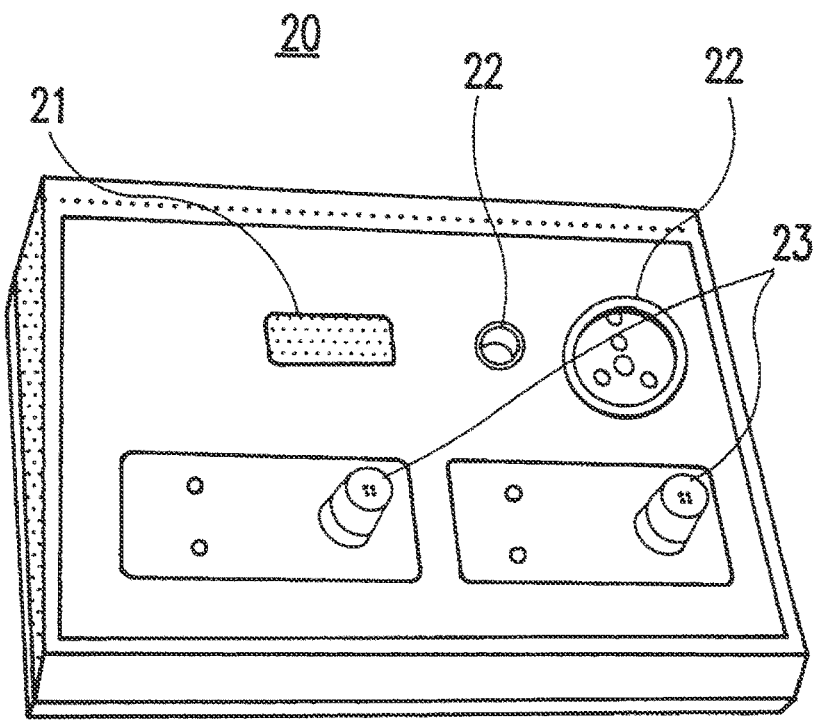
FIG. 2 depicts a recharger for charging the handheld tool shown in FIG. 1.

FIG. 2 depicts recharger 20, in accordance with an embodiment, that is used for receiving and charging batteries of the tool 1. Recharger 20 may be coupled to an ordinary AC outlet (e.g., 120V/60A), such as via a cord (not shown). Tool 1 can be inserted into or otherwise coupled with recharger 20 and charged, as required. Alternatively, the recharger 20 can charge rechargeable batteries that are insertable into the laser tool 1. A rechargeable battery can be connected to the laser tool 1, such as via threading the battery onto a threaded end of the laser tool 1.

The recharger 20 has a light emitting diode meter 21 to measure the laser energy output of tool 1, a plurality of probe sensors 22, and battery mounts 23. The batteries can be charged by the recharger 20 by removing them from the laser tool 1 and threading them to one of the battery mounts 23 on the recharger 20.

Figure 3:
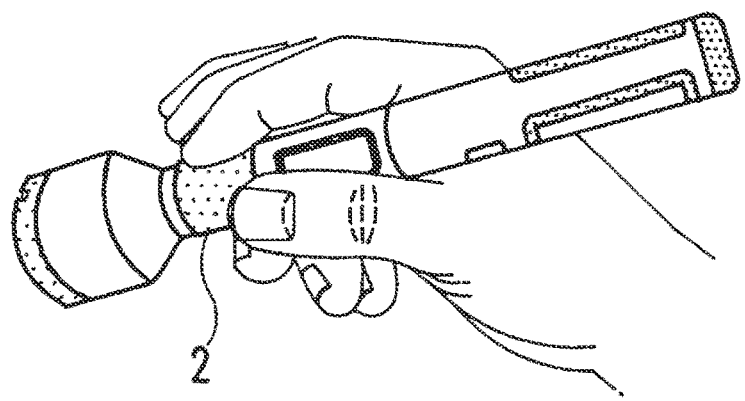
FIG. 3 illustrates the handheld laser tool of FIG. 1 being held by an operator.

With reference to FIG. 3, in operation tool 1 can be activated by the switch 2. Activation of tool 1 occurs by depressing the switch 2, such as by squeezing with the hand or fingers as shown in FIG. 3. Once the laser is activated, no further pressure may be required on the annular switch 2 to continue the cycle. That is, the laser of tool 1 remains activated for one 33-second cycle or until the annular switch 2 is depressed again.

Figure 4:
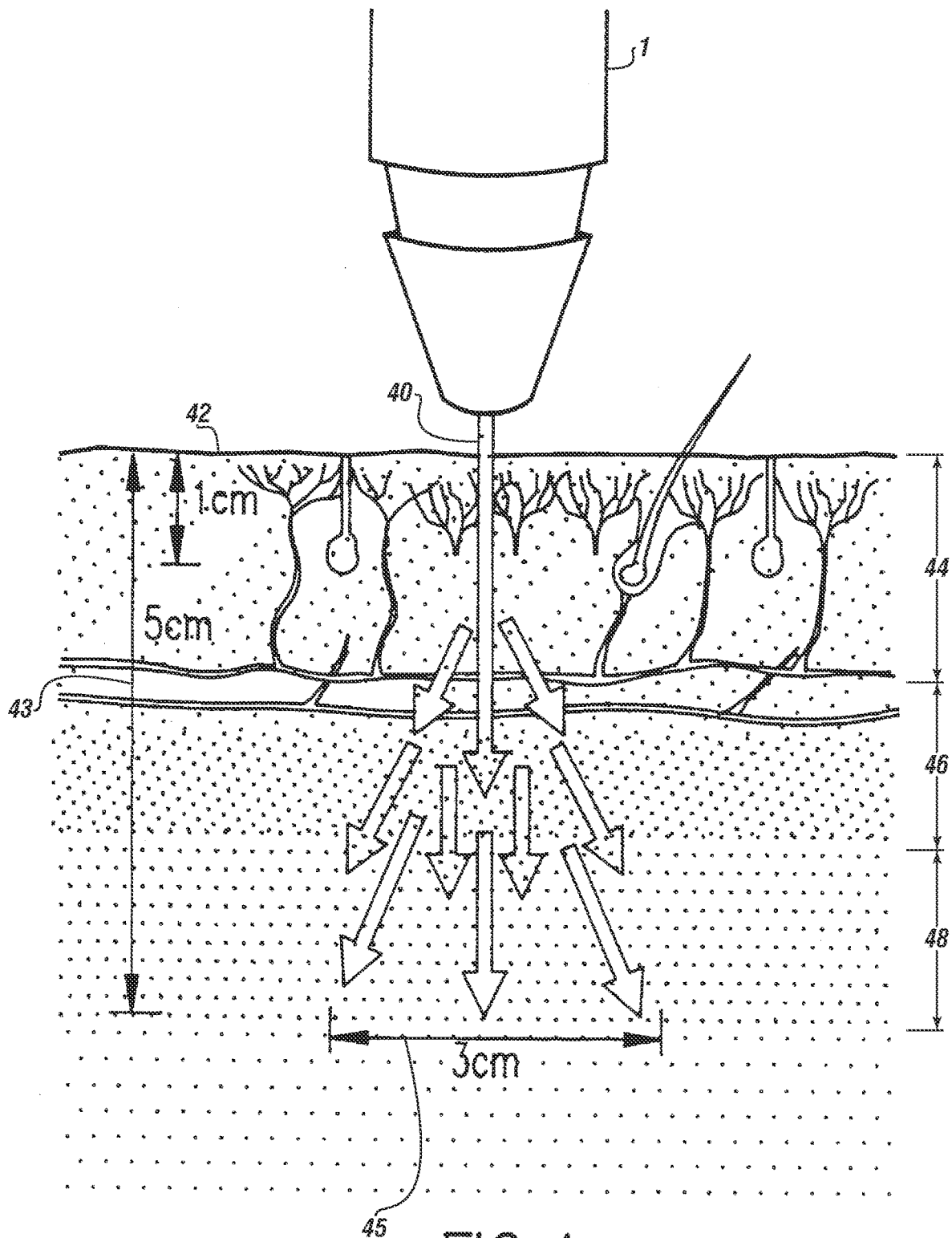
FIG. 4 illustrates an example of tissue being treated with the handheld tool of FIG. 1.

FIG. 4 depicts tool 1 emitting laser light 40, which penetrates skin surface 42. As shown, laser light 40 penetrates epidermis 44, dermis 46, and subcutaneous layers 48, entering the flexor tendons and surrounding tissues. The wavelength range of the laser light may be from 800-870 nm, and preferably 830 nm, such that the beam of laser light 40 does not lose appreciable power when directed through a patient's skin. Thus, using such a wavelength allows the device to probe deeply with a low power laser. Photons of the laser light 40 impact the cells and stimulate nerves, which can improve micro-circulation; thereby, bringing increased oxygen and blood flow to a problem area. The laser light 40 beam may also act to block pain enzymes and activates synthesis of endorphin enzymes.

Treatment can be administered by placing the head of the laser tool 1 in contact with shaved skin over an affected area. Alternatively, a clear laser transmission gel can be used over wounds and unshaven skin. The transmission gel can be copiously applied to the treatment area. A clear plastic cover can be placed over the head of the laser prior to placing the laser in contact with the patient's skin and/or the gel. Thereafter, the laser tool 1 can be activated and held steady during the treatment period. Then, the laser tool 1 can be rotated (e.g., 60) degrees and the tool 1 activated again. The tip of the laser probe can be in complete and direct contact with the surface of the skin during treatment. The laser light 40 can be directed into the surface of the skin 42 at a right angle relative to the surface of the skin 42. In some embodiments, the laser light 40 penetrates the surface of the skin 42 to a maximum depth of from 3 to 5 cm.

Some potential biological effects of laser light include cell growth stimulation (connective tissue, tendons, bone, muscles and nerves), cell regeneration (connective tissue, tendons, bone, muscles and nerves), revascularization (oedema inhibition, contraction loosening, anti-inflammatory, increase of microcirculation), anti-inflammatory (increases the microcirculation and reduces the ability of the lymphocytes to react to antigen stimuli, for all tissues), stimulation of nerve function (nerve tissue, increases the amplitude of the action potential, inhibition of clonus, acupuncture treatment), and reduction in the formation of fibrous tissue (following tissue damage the formation of fibrous tissue is reduced/retarded, e.g., after burns). Some potential clinical effects of laser light include promotion of healing (as mentioned above revascularization/cell regeneration and cell growth stimulation, for all tissues), pain-relief (nerve tissue, tendons, periosteum, muscles and connective tissue). A variety of different tissue structures can be treated using laser light, including skin, subcutaneous tissues and mucous membranes; muscles; tendons; the vascular system; the nervous system; periosteum; and joints. For acute and chronic diseases, the treatment indicators may include inflammation, necrosis/gangrene, contusions, oedema, haematomas, strains, sprains, avulsions, ruptures, dislocations, contractures, atrophy, paresis/paralysis, arthritis and postoperative patients.

Figure 5:
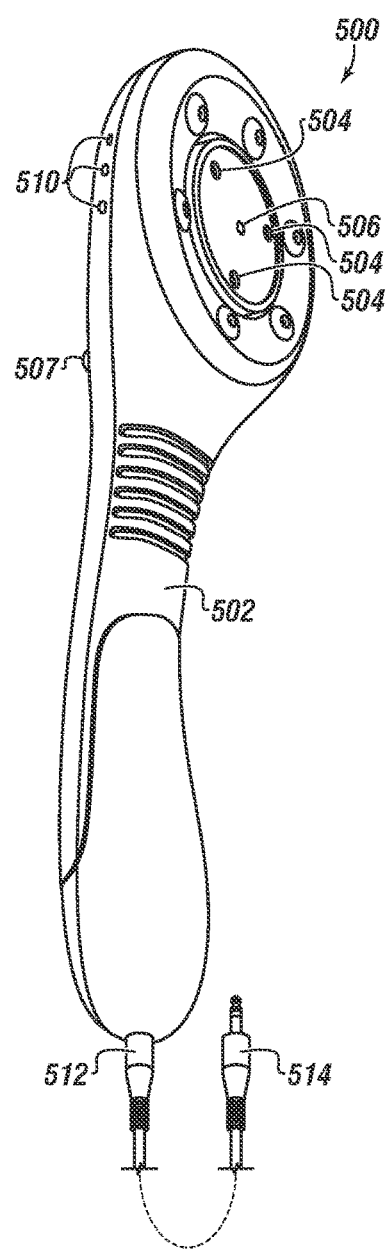
FIG. 5 depicts another handheld laser emitting tool.

The table shown in FIG. 5 of the '436 Patent illustrates general treatment dosages and is useful as a guide. The suggested dose can be adjusted according to the progress of the condition and the depth of penetration required. The table shown in FIG. 6 of the '436 Patent illustrates conditions that may respond to LLLT and for various tissue lesions with examples of individual types of tissue.

Low Level Laser Therapy with Cannabidiol

Some embodiments of the present disclosure include systems and methods for using LLLT in combination with CBD to provide therapeutic treatment to the skin or other tissues. In some such embodiments, the LLLT is performed using the handheld laser light tool disclosed in the '436 Patent. In some embodiments, an 830 laser available from MICROLIGHT® Corporation of America, of Sugarland, Tex., is used to apply the laser light disclosed herein. While the methods and systems described herein refer to the use of CBD oil, the present disclosure is not limited to a particular form of CBD and may include the use of CBD salves, CBD balms, or other topical forms of CBD. Table 1, below, sets forth some operational parameters of one exemplary laser usable herein (the 830 laser).

TABLE 1

830 Laser - Technical Information

| | Triple Probe | Single Probe |
|---|---|---|
| Laser Diodes | GaAlAs (3), Visible Red LED (1) | GaAlAs (1) |
| Wavelength | 830 nm NIR | |
| Laser Output | 30 mW × 3 = 90 mW | 90 mW |
| Laser Energy Delivered | 1 Joule per laser diode × 3 laser diodes = 3 Joules per treatment cycle | 3 Joules per treatment cycle |
| Beam Configuration | Elliptical (1 mm × 3 mm) × 3 | Elliptical (1 mm × 3 mm) |
| Input Voltage/Frequency for Battery Charger | 100/240 volts AC 47/63 Hz - 0.5 A | |
| Output Voltage of Battery Charger | 5 Volts DC, maximum | |
| Output Watts/Amps of Battery Charger | 15 Watts-3.0 Amps. | |
| Weight | ~230 grams | ~130 grams |
| Dimensions | 8.75 inches long and 2.8 inches wide and 1 inch high (22 cm long × 7 cm wide × 2.5 cm high | 7 inches long and 0.8 inches wide and 1 inch high (18 cm long × 2 cm wide × 2.5 cm high) |

In some embodiments, the laser probe described in Table 1 is calibrated to a fixed output of 90 mW±10%, a maximum of 99 mW (33 mW each diode). The triple probe version of the laser described in Table 1 contains three GaAlAs continuous wave diodes operating in the near infrared at a wavelength of 803 nm with a power output measured at 30 mW for each diode with a non-collimating beam with dimensions of approximately 1 by 3 millimeters at the lens. In some embodiments, the laser probe described in Table 1 having the single probe contains one GaAlAs continuous wave diode operating in the near infrared at a wavelength of 830 nm with a power output measured at 90 mW with a non-collimating beam with dimensions of approximately 1 by 3 millimeters at the lens.

Figure 6A:
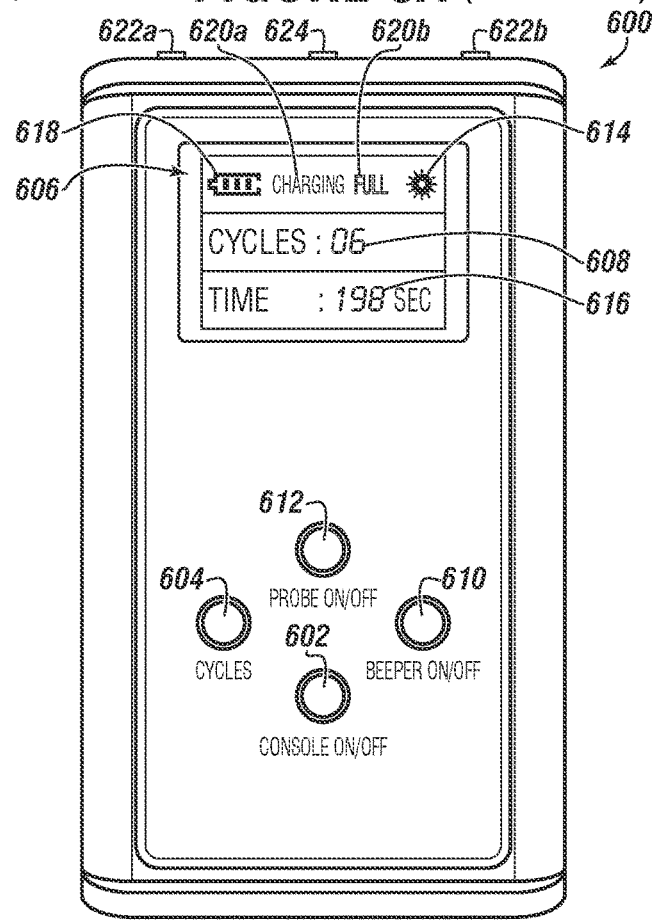
FIG. 6A depicts a tool console for controlling the laser emitting tool of FIG. 5.
Figure 6B:
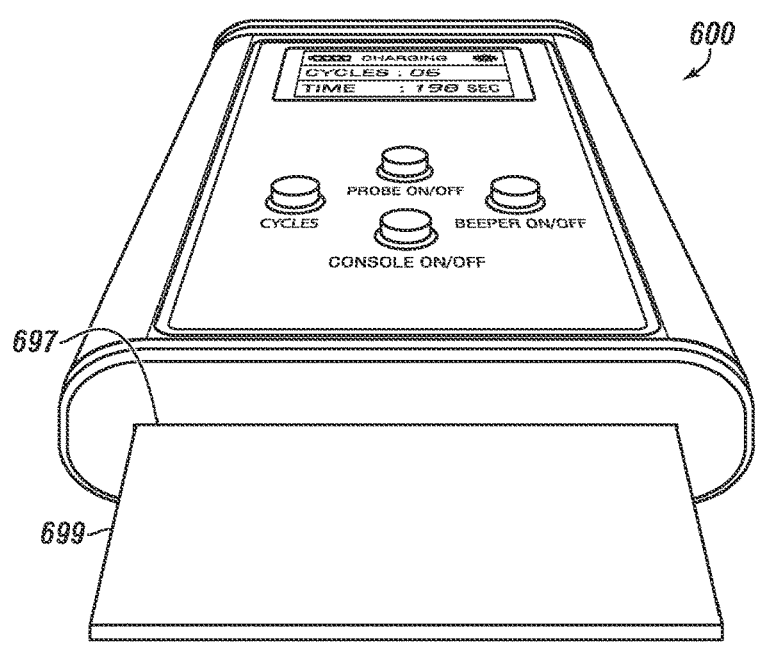
FIG. 6B depicts another tool console for controlling the laser emitting tool of FIG. 5.

With reference to FIGS. 5-6B, an exemplary laser tool that may be used in the present method will be described. FIG. 5 depicts handheld laser tool 500. Tool 500 includes handle 502, allowing a user to hold tool 500 to perform the treatments disclosed herein. Tool 500 includes diodes 504 (here three diodes are shown) for emitting laser light from tool 500 during treatment of tissue. In one exemplary embodiment, diodes 504 may be 30 mW diodes that emit laser light of an 830 nm wavelength. While shown as including three diodes, the laser light emitting tools disclosed herein are not limited to having three diodes, and may include more or less than three diodes. Tool 500 includes guide light 506, which may be a visible light that can be used to aim the tool 500. For example, guide light 506 may be an LED (or another light) that can direct light onto the skin such that the light reflects back off of the skin, providing the user with an indication of where the tool 500 is pointing and, in particular, wherein the diodes 504 are pointing. This can allow the user to ensure that the tool 500 is being aimed at the proper location on the skin where the ailment is located. Tool 500 can include a visual alert 507, such as a flashing light, that is indicative of when the laser is activated. Tool 500 can include ventilation 510 to cool the tool 500. Tool 500 includes cord 512 with strain relieve features incorporated therein and with a DC plug 514 thereon for connecting with (plugging into) a console probe jack.

FIG. 6A depicts tool console 600. Console 600 includes various buttons for control of the console 600 and tool 500. For example, console 600 includes on/off button 602 for turning the console 600 on and off. Console 600 includes beeper on/off button 610 to activate or deactivate the emission of an audible alert during a treatment (i.e., during emission of laser light from tool 500). Console 600 includes probe on/off button 612 for activating and deactivating the emission of laser light from the laser tool 600. Console 600 includes cycle button 604 for controlling the number of cycles in which the laser is activated (i.e., controlling the number of sequential cycles in which the laser tool 500 is activated to emit laser light). For example, cycle button 604 may be used to select a number of cycles that the console 600 activates the tool 500 to emit laser light during a treatment. In one example, a treatment may include 55 cycles, each lasting 33 seconds, such that the total time in which laser light is emitted is 1,815 seconds (30.25 minutes), i.e., 55×33. In such embodiments, there is a period of time between the occurrence of each cycle where laser light is not emitted from tool 500, referred to herein as a "pause time." In embodiments where the emission of laser light is not interrupted (i.e., is constant), there is no pause time. In embodiments where the emission of laser light is interrupted by pause times (i.e., is intermittent), the length of time for which the laser light is emitted from the tool 500 may be any desirable length of time, such as 33 seconds. Furthermore, the length of time for which the laser light is emitted from the tool 500 may vary from one cycle to the next within a single treatment. For example, within a single treatment, laser light may be emitted for 33 seconds, followed by a pause time, and then laser light may be emitted for 16 seconds, followed by a second pause time, and so forth. In the same or similar manner, the length of the pause time for which the laser light is not emitted from the tool 700 may vary from one cycle to the next within a single treatment. As would be understood by one skilled in the art, the existences of, length of, and consistency of the pause may be varied; the length of the cycle time may be varied; the total length of the treatment may be varied; and the wavelength of the laser light may be varied.

Console 600 includes display 606. Display 606 presents information about console 600 and the treatment parameters (e.g., the length of the cycles, the length of the pause times, the total length of the treatment, and the wavelength of the laser). For example, a user can increase or decrease the number of cycles in a treatment, and display 606 will display the number of currently selected cycles 608. Display 606 also presents activation alert symbol 614 to indicate when the laser tool 500 is activated and emitting laser light, time

616 indicating the time remaining in the treatment, battery status 618 indicating the degree of charge of a battery of console 600, and charging status 620a and 620b indicating whether or not the console battery is charging, 620a, or whether the charge is full, 620b. Console 600 also includes probe jacks 622a and 622b for connecting console 600 to one or more tools 500, and DC jack 624 for connecting console 600 to recharge the battery thereof. In some embodiments, a battery charger can be connected into the DC jack of the console 600.

FIG. 6B depicts another embodiment of a console, console 600, that is substantially identical to that shown in FIG. 6A. However, in FIG. 6B console 600 is shown having a laser card 699 inserted therein. Console 600 includes a card reader 697 for reading card 699. Card 699 may be a card having computer executable instructions stored therein, in a non-transitory form, that instruct the console 600 regarding the particular treatment cycle to be used. For example, each ailment may be associated with a different treatment cycle that has a particular number of cycles. The card 699 may be used to instruct the console 600 to activate a laser emitting tool in accordance with a particular pattern of cycles. The consoles disclosed herein can include processors capable of executing the computer instructions of the card.

In some embodiments, the laser tool 500 is a handheld, non-invasive, non-thermal, low energy, therapeutic laser emitting tool. In embodiments, the laser tool 500 is capable of producing infrared (invisible) laser light at the 830 nm wavelength, and is classified by the Federal Drug Administration (FDA) as a Class IIIB medical device. The laser tool 500 can emit laser light that penetrates relatively deeply into tissue, such as at a penetration of approximately 5 cm, with an approximately 3 cm lateral spread. The penetration depth 43 and lateral spread 45 of laser light 40 is illustrated in FIG. 4. The "penetration depth" refers to the furthest depth into the tissue (as measured from the surface of the tissue 42) to which the laser light propagates. The "lateral spread" refers to the greatest dimensional magnitude of the laser light within the tissue that is not the penetration depth. That is, within a cartesian coordinate system with the penetration depth coextensive or parallel with the y-axis, the lateral spread refers to the greatest dimensional magnitude of the laser light within the tissue along the x-axis and z-axis.

Once delivered, the light energy may promote the process of photo-bio-stimulation, promoting photochemical reactions in the human skin that produce an increase in the cellular metabolism rate that expedites cell repair and the stimulation of the immune, lymphatic and vascular systems. The LLLT treatment may reduce pain, inflammation, edema and overall healing time. Without being bound by theory, low level lasers supply energy to the body in the form of photons of light that do not create heat within the tissue. Light is transmitted through the skin's layers at all wavelengths in the visible range. However, light waves in the near infrared ranges penetrate the deepest of all light waves in the visible spectrum. When low level laser light waves penetrate deeply into the skin, they optimize the immune responses of blood. This can have both anti-inflammatory and immunostimulant effects.

Figure 7A:
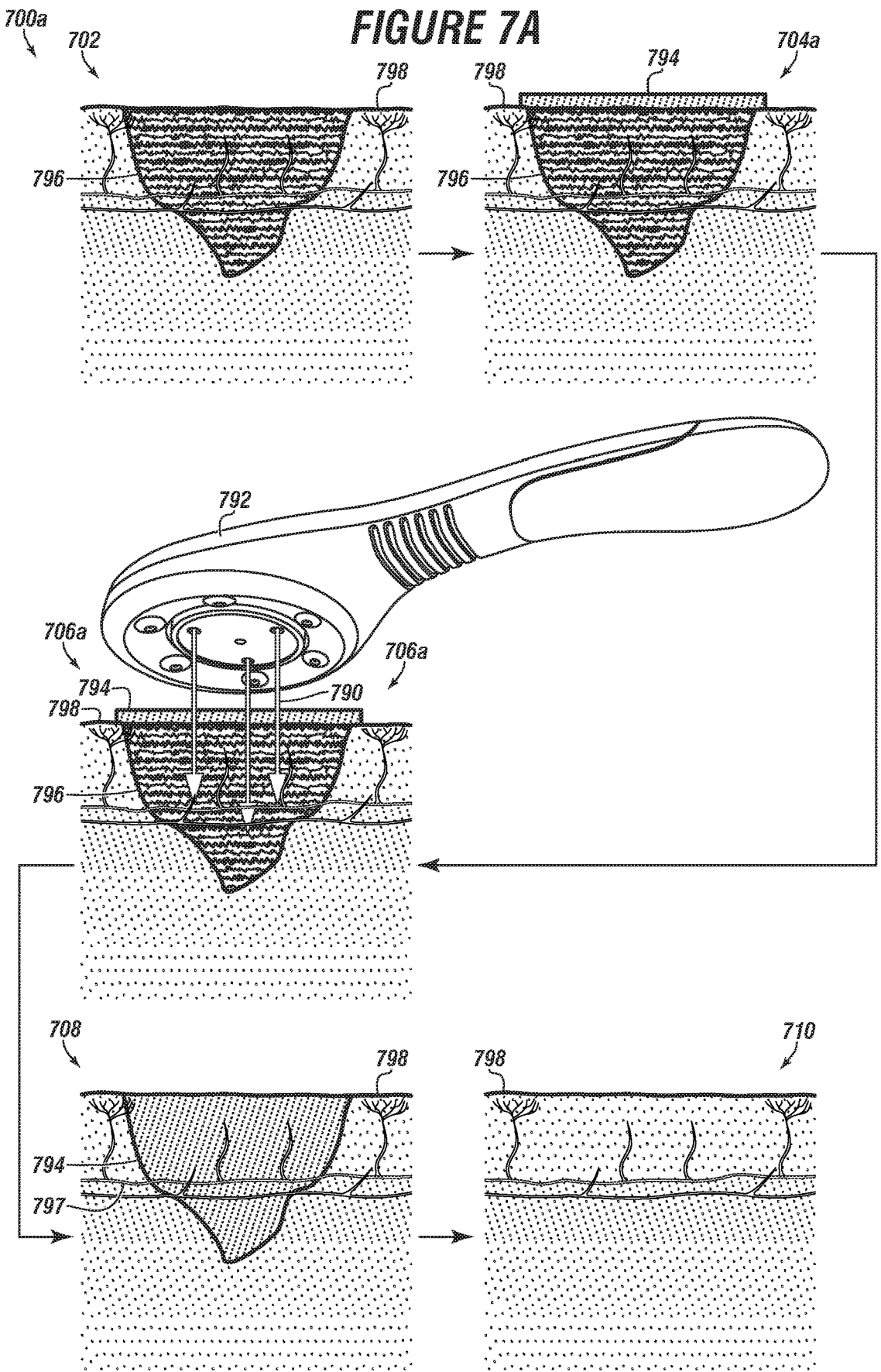
FIG. 7A-7C depict methods of applying CBD with a laser, optionally using an applicator pad or gauze.

In some embodiments, the method includes applying CBD to the skin using laser light. Some embodiments include applying CBD to the skin of the patient at the affected area. In some embodiments, applying CBD to the skin includes applying the CBD to an applicator pad and/or gauze, and then applying the applicator pad and/or gauze to the skin of the patient at the affected area. In other embodiments, the method includes apply the CBD directly to the skin without the use of an applicator pad and/or gauze. The affected area is an area of skin to be treated, such as an area of the skin where a patient is experiencing pain, inflammation, or any other ailments, such as any of the ailments disclosed in the '436 Patent. In some embodiments, the CBD used herein is pure, containing no fillers or additives. With the CBD applied to the skin of the patient, the method includes applying laser light to the area of the skin upon which the CBD is applied. The laser light may be applied to the skin in accordance with the methods disclosed in the '436 Patent. In one embodiment, the laser tool is activated to apply laser light to the skin for a period of time, such as for 10 minutes or about 10 minutes. The laser light may be applied to the skin in cycles, for example in cycles of 33 seconds. In one example, the laser light is applied to the skin in 18 cycles that last approximately 33 seconds each, with a time period (pause time) between each cycle in which no laser light is applied to the skin. In such an embodiment, the total time in which laser light is applied to the skin is about 9.9 or 10 minutes. In some embodiments, the application of laser light to the skin applies 54 joules of laser light to the skin. The laser light may have a wavelength of, for example, 830 nanometers and have 90 milliwatts of energy. With reference to FIG. 7A, an embodiment of the method disclosed herein is described. Method 700a includes step 702 of identifying an area for treatment 796 on a patient's skin 798. Next, method 700a includes a step 704a of applying CBD 794 onto the skin 798 at the area for treatment 796. In some embodiments, the CBD 794 is applied to the skin and allowed to be remain on the skin for a residence time (e.g., from 5 to 30 minutes) prior to application the laser light thereto. Next, method 700a includes step 706a of irradiating the area for treatment 796 and irradiating the CBD 794 applied thereto with laser light 790 from laser tool 792. In some embodiments, the laser tool 792 is held above the skin, at a distance from the surface of the skin. In some embodiments, the laser tool 792 is attached to the patient (e.g., via straps), such that the diodes of the laser tool 792 are positioned to emit light onto the area for treatment 796. As shown in step 708, the irradiation causes at least some of the CBD 794, or components thereof, to penetrate into area for treatment 796. Area for treatment 1296 may be an area where, for example, the patient is experiencing pain and/or inflammation. The CBD 794, or components thereof, penetrate into skin 798 to a penetration depth sufficient that at least some of the CBD 794, or components thereof (e.g., ions thereof), penetrate into or otherwise enter into blood vessels 797 within the skin 798. These steps may be repeated, as needed, until the skin 798 is free of the ailment, as shown in step 710.

Figure 7B:
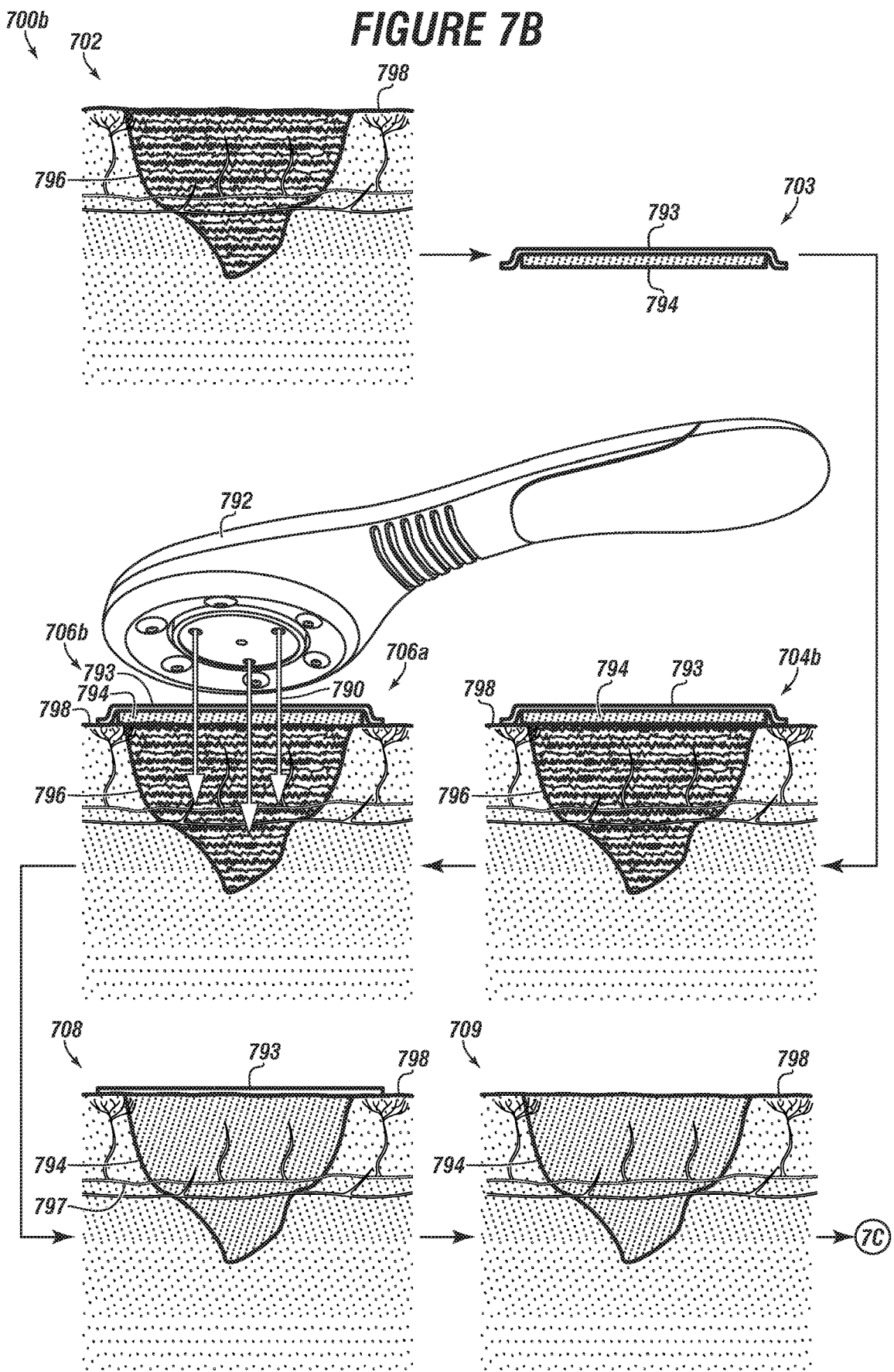
Figure 7C:
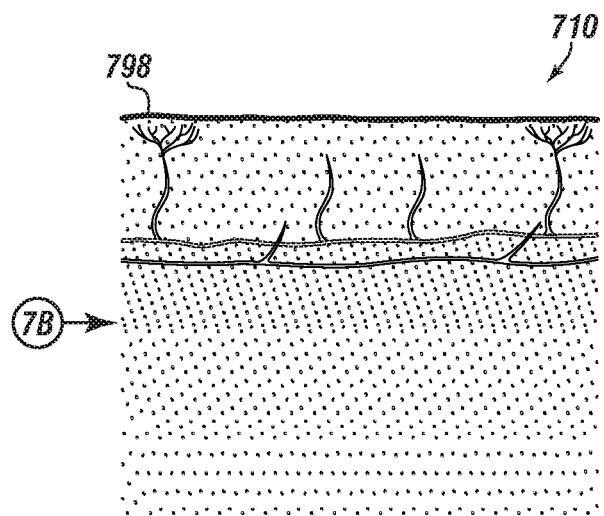

With references to FIGS. 7B and 7C, another embodiment of the method disclosed herein is described. Method 700b includes step 702 of identifying an area for treatment 796 on a patient's skin 798. Next, method 700b includes a step 703 of applying CBD 794 to an applicator pad 793. Next, method 700b includes a step 704b of applying the applicator pad 793 with the CBD 794 onto the skin 798 at the area for treatment 796. Next, method 700b includes step 706b of irradiating the area for treatment 796 and irradiating the applicator pad 793 and CBD 794 applied thereto with laser light 790 from laser tool 792. As shown in step 708, the irradiation causes at least some of the CBD 794, or components thereof, to penetrate into area for treatment 796. The CBD 794, or components thereof, penetrate into skin 798 to a penetration depth sufficient that at least some of the CBD 794, or components thereof (e.g., ions thereof), penetrate into or otherwise enter into blood vessels 797 within the skin 798. Next, method 700b includes step 709 of removing the applicator pad 793. These steps may be repeated, as needed, until the skin 798 is free of the ailment, as shown in step 710.

The use of LLLT with the CBD applied to the skin provides a transdermal delivery system or method, such that the CBD is propelled by the laser light into the skin to a depth beyond the surface of the skin. In contrast to oral injection and inhalation of CBD, the present method provides the CBD to specific localized sites for treatment; thereby, avoiding adverse effects of medicating localized ailments with generalized treatments and providing for a more concentrated dosage of the CBD where the CBD is needed. In comparison to topical application of CBD without the use of LLLT, the present method is capable of delivering the CBD more deeply into the patient's tissue to address ailments that are not just at the skin's surface, such as joint pain. In some embodiments, the ability to cause the CBD to penetrate more deeply into the skin tissue reduces or eliminates residual CBD coatings or films on the skin after such treatments.

In some embodiments, each treatment session lasts 20 minutes or less, and ailments may be successfully treated in 20 treatments or less, such as from 4 to 18 treatments, or from 5 to 10 treatments.

Some benefits and/or effects that may be attained using the methods disclosed herein include: bio-stimulation, including improved metabolism and increased cell metabolism; improved blood circulation and vasodilatation; analgesic effects; anti-inflammatory and anti-edematous effects; stimulation of wound healing; relief of acute and chronic pains; increase in the speed, quality and tensile strength of tissue repair; increases in blood supply; stimulation of the immune system; stimulation of nerve function; development of collagen and muscle tissue; generation of new and healthy cells and tissue; promotion of faster wound healing and clot formation; and reduction in inflammation.

The method disclosed herein may be used to address the following ailments and/or conditions: acupuncture points; arthralgia/arthritis; back pain; bursitis; carpal tunnel syndrome; fibromyalgia; herniated/bulging discs; knee pain; injuries; migraine headaches; muscle pains/spasms; neck pain/whiplash; neuralgia; nerve pain/radiculopathy; plantar fasciitis; post-operative pain; sprains/strains; swelling; TMJ pain/dysfunction; tendonitis; tennis elbow; trigger points and wound healing.

While described for use in specific ailments, one skilled in the art would understand that the present methods and apparatus may be used to penetrate CBD into the skin for other ailments as well as for non-ailment related uses. While described for use on humans, one skilled in the art would understand that the present methods and apparatus may be used on other animals, such as dogs. While the CBD is described as being applied to the skin, one skilled in the art would understand that the present methods and apparatus may be used to penetrate CBD into other tissues.

Without being bound by theory, the application of CBD using laser light, as disclosed herein, may be used as pain medicine. Iontophoresis involves the forcing of a compound through the skin, going from an area of one electric charge to an area with an opposite electric charge. This involves using electrical charge generators applied to an external compound to drive that compound through the skin to an area having an opposite electrical charge. Electrons (produced by a charge generator) and photons are both forms of electromagnetic energy. Devices used to produce such emissions of electromagnetic energy may be referred to as "voltage generators." The addition of energy imparted to skin cells, circulatory tissue (blood vessels), extra-cellular space (lymphatic drainage), and intra-cellular components, can change the electrical charge of the tissue. Photon energy is believed to increase the release of nitric oxide from cells that line the walls of small blood vessels, and to desensitize nerve tissue receptors, as well as affect other intra-cellular functions, indicating that electrical charges that influence these effects are altered. Photon therapy, as disclosed herein, can result in the iontophoresis of compounds (such as CBD oil) through the skin and into other tissues. Using a laser with a wavelength of 830 nm can affect tissues at a depth of 2-4 inches. In some embodiments, the wavelength of the laser light is consistently maintained at 830 nm throughout the duration of the treatment. That is, during the entirety of the treatment, only light of 830 nm is emitted from the laser light tool. In some embodiments, the wavelength of the laser light is consistently maintained at about 830 nm throughout the duration of the treatment. As used herein, "about 830 nm" refers to light ranging from 825 nm to 835 nm, or from 827 nm to 833 nm, or from 829 nm to 831 nm, or light that is 830 nm.

In some embodiments, the laser light and CBD and laser light treatment disclosed herein can be used to treat myofascial trigger points. For example, CBD may be applied to the skin and allowed to rest on the skin for a residence time of about five minutes to thirty minutes, after which laser light is applied to the skin and CBD. In some embodiments, the laser light and CBD treatments disclosed herein are followed by heat and/or stretching treatments of the muscles. In some embodiments, the CBD and laser light treatments disclosed herein reduce trigger point tenderness to latent or essentially latent levels. In two exemplary embodiments, the laser light and CBD and laser light treatment disclosed herein can be used to treat myofascial pain and Parkinson's, or widespread fibromyalgia and numerous trigger points. Two exemplary CBD products that may be used in accordance with the methods disclosed herein are Kannaway liquid (1500 mg) and Kannaway Salve (500 mg), both commercially available from Kannaway.

Although the present embodiments and advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for therapeutic application of laser and cannabidiol to skin tissue, the method comprising:
applying cannabidiol onto the skin tissue; and
irradiating the skin tissue and the cannabidiol applied to the skin tissue with a laser light, wherein the laser light has a wavelength ranging from 800 nm to 870 nm that is sufficient to cause absorption of at least some of the cannabidiol into the skin tissue.

2. The method of claim 1, wherein the wavelength is sufficient to cause absorption of at least some of the cannabidiol into a bloodstream within the skin tissue.

3. The method of claim 2, wherein the laser light has a wavelength of about 830 nm.

4. The method of claim 1, wherein the applying of the cannabidiol onto the skin tissue comprises applying the cannabidiol onto an applicator pad or gauze, and then applying the applicator pad or gauze onto the skin tissue.

5. The method of claim 1, wherein after applying the cannabidiol onto the skin tissue and prior to irradiating the skin tissue and the cannabidiol, the cannabidiol is resident on the skin tissue for a residence time.

6. The method of claim 1, wherein the skin tissue is irradiated with the laser light in a plurality of intermittent cycles over a treatment period.

7. The method of claim 6, wherein the treatment period is from 4 to 18 minutes, and wherein each of the intermittent cycles has a duration of from 15 to 40 seconds.

8. The method of claim 1, wherein the cannabidiol absorbs into the skin tissue to a penetration depth ranging from 3 to 5 cm.

9. The method of claim 1, wherein the laser light has a lateral spread of from 1 to 3 cm within the skin tissue.

10. The method of claim 1, wherein the method results in: bio-stimulation, including improved metabolism and increased cell metabolism; improved blood circulation and vasodilatation; analgesic effects; anti-inflammatory and anti-edematous effects; stimulation of wound healing; relief of acute and chronic pains; increase in the speed, quality and tensile strength of tissue repair; increases in blood supply; stimulation of the immune system; stimulation of nerve function; development of collagen and muscle tissue; generation of new and healthy cells and tissue; promotion of faster wound healing and clot formation; or reduction in inflammation.

11. The method of claim 1, wherein the method provides therapeutic treatment for: arthralgia/arthritis; back pain; bursitis; carpal tunnel syndrome; fibromyalgia; herniated/bulging discs; knee pain; injuries; migraine headaches; muscle pains/spasms; neck pain/whiplash; neuralgia; nerve pain/radiculopathy; plantar fasciitis; post-operative pain; sprains/strains; swelling; TMJ pain/dysfunction; tendonitis; tennis elbow; trigger points or wound healing.

12. The method of claim 1, wherein the laser light is provided by a laser light system, the laser light system comprising:
a laser emitting tool including at least one diode that emits the laser light; and
a tool console, wherein the tool console is in data communication with the laser emitting tool and transmits control signals to the laser emitting tool to actuate emission of the laser light.

13. The method of claim 12, wherein the laser emitting tool comprises a guide light that emits a visible light, the method comprising using the guide light to aim the at least one diode at a location on the skin tissue.

14. The method of claim 12, wherein operation of the console is controlled by a card that includes computer executable instructions stored therein, in a non-transitory form, wherein the computer executable instructions instruct the console regarding parameters for a treatment.

15. The method of claim 14, wherein the parameters include a number of intermittent cycles of the laser light emitted during the treatment, a length of time for each cycle during the treatment, a total time of the treatment, or combinations thereof.

16. The method of claim 1, further comprising performing a grid treatment cycle on the skin tissue, the grid treatment cycle comprising:
defining a grid on the skin tissue, the grid comprising a plurality of discrete portions of the skin tissue;
applying the cannabidiol onto each discrete portion of the skin tissue within the grid; and
irradiating each discrete portion of the skin tissue having the cannabidiol applied thereon.

* * * * *